United States Patent [19]

Capiris et al.

[11] Patent Number: 5,288,896

[45] Date of Patent: Feb. 22, 1994

[54] 3,5-DI-T-BUTYL-4-HYDROXYLPHENYLME-THYLHYDROXYLAMINES AND THEIR DERIVATIVES, PHARMACEUTICAL COMPOSITIONS, AND METHODS OF USE THEREFOR

[75] Inventors: Thomas Capiris, Plymouth; David T. Connor; Jagadish C. Sircar, both of Ann Arbor, all of Mich.

[73] Assignee: Warner-Lambert Company, Morris Plains, N.J.

[21] Appl. No.: 821,103

[22] Filed: Jan. 15, 1992

[51] Int. Cl.$^5$ ............................................. C07C 271/00
[52] U.S. Cl. ...................................... 560/27; 564/28; 564/170; 564/321; 564/52; 560/8
[58] Field of Search .............. 560/8, 27; 564/28, 52, 564/170, 321; 514/613, 655, 657, 716, 741, 825, 886, 887

[56] References Cited

FOREIGN PATENT DOCUMENTS 185158 6/1986 European Pat. Off. .

OTHER PUBLICATIONS

Derwent Abstract No. 91-112647/JO 3052849 1989.
Derwent Abstract No. 90-181443/25 *JO 310263.
Derwent Abstract No. 91-112647/16*JO 3052849.

Primary Examiner—Paul J. Killos
Assistant Examiner—D. D. Carr
Attorney, Agent, or Firm—Ronald A. Daignault; Elizabeth M. Anderson

[57] ABSTRACT

The present invention is a novel compound which is a 3,5-di-t-butyl-4-hydroxyphenylmethylhydroxylamine or derivative thereof and a pharmaceutically acceptable acid addition or base salt thereof, pharmaceutical composition and methods of use therefor. The invention compounds are now found to have activity as inhibitors of one or both of cyclooxygenase and 5-lipoxygenase providing treatment of conditions advantageously affected by such inhibition including inflammation, arthritis, pain, fever, and the like.

17 Claims, No Drawings

3,5-DI-T-BUTYL-4-HYDROXYLPHENYLMETHYL-HYDROXYLAMINES AND THEIR DERIVATIVES, PHARMACEUTICAL COMPOSITIONS, AND METHODS OF USE THEREFOR

BACKGROUND OF THE INVENTION

The present invention is a novel compound which is a 3,5-di-t-butyl-4-hydroxyphenylmethylhydroxylamine or derivative thereof and a pharmaceutically acceptable acid addition or base salt thereof, pharmaceutical composition and methods of use therefor. The invention compounds are now found to have activity as inhibitors of one or both of cyclooxygenase and 5-lipoxygenase providing treatment of conditions advantageously affected by such inhibition including inflammation, arthritis, pain, fever, and the like. Thus, the present invention is also a pharmaceutical composition or method of use thereof.

The following are references disclosing related derivatives.

U.S. Pat. No. 4,673,692 or EP Application 0185158 discloses diphenylmethylimine derivatives where one of the phenyls is a 3,5-di-t-butyl-4-hydroxyphenylmethyl moiety useful for the treatment of inflammation, pain, or rheumatism.

JO 3109263 described in Derwent Abstract No. 91-181443/25 discloses 2,6-di-t-butyl-4-[amino(phenyl)-methylene]-2,5-cyclohexadien-1-ones and derivatives including substitutions on both the amino and phenyl groups for use as inhibitors of arachidonic acid, cyclooxygenase and lipoxygenase inhibitors.

JO 3052849 discloses oxime intermediates providing 3,5-di-t-butyl-4-hydroxy-diphenylmehyl amine derivatives as antiinflammatory agents, antirheumatics, and analgesic agents (see Derwent Abstract No. 91-112647/16.

U.S. Pat. No. 5,066,679 discloses di-t-butyl substituted phenolic thioalkylamides as inhibitors of 5-lipoxygenase.

These disclosures differ structurally from the present invention by the absence of the combination of a 3,5-di-t-butyl-4-hydroxyphenyl and a selected optionally substituted phenyl, thienyl, furanyl, isoxazolyl, or heterocyclic group through a methylene bridge where the methylene is further substituted by a substituted hydroxylamine.

SUMMARY OF THE INVENTION

The present invention is a compound of the Formula (I)

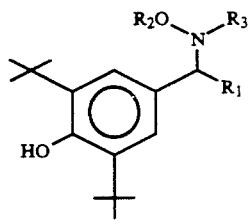

or a pharmaceutically acceptable salt thereof; wherein
$R_1$ is
1) hydrogen;
2) methyl;
3) phenyl optionally substituted by from one to three of i) hydrogen, ii) halogen, iii) trifluoromethyl, iv) lower alkyl, v) lower alkoxy, and vi) hydroxy;
4) 2- or 3-thienyl;
5) 2 or 3-furanyl;
6) isoxazolyl;
7) 5 or 6 heterocycle wherein the heterocycle is a saturated ring having one to three heteroatoms selected from nitrogen, oxygen and sulfur;

$R_2$ is
1) hydrogen;
2) alkanoyl of from two to four carbon atoms; or
3) lower alkyl;

$R_3$ is
1) hydrogen;
2) lower alkyl;
3) alkanoyl of from two to four carbon atoms;
4) $CXR_4$ wherein X is i) oxygen or ii) sulfur and $R_4$ is $NR_5R_6$ wherein $R_5$ is hydrogen and $R_6$ is hydrogen, lower alkyl, or $COOR_7$ wherein $R_7$ is lower alkyl; or
5) $COR_7$ or $COOR_7$ wherein $R_7$ is as defined above.

The present invention is also a pharmaceutical composition for the treatment of conditions advantageously affected by the inhibition of one or both 5-lipoxygenase and cyclooxygenase which comprises an amount effective for the treatment of the condition of a compound of Formula I as defined above or the pharmaceutically acceptable salt thereof together with a pharmaceutically acceptable carrier.

Compounds of this invention are inhibitors of the synthesis of the products of one or both of the enzymes 5-lipoxygenase and cyclooxygenase, and are for the treatment of the conditions meant to include rheumatoid arthritis, osteoarthritis, other inflammatory conditions, psoriasis, pain, allergic diseases, asthma, inflammatory bowel disease, GI ulcers, cardiovascular conditions including ischemic heart disease and atherosclerosis, and ischemia-induced cell damage, particularly brain damage caused by stroke. These conditions can also include acne, sunburn, psoriasis, and eczema. Such conditions are exemplary in nature and are in no way meant to limit the scope of the invention.

Thus, the present invention is also a method for treatment of the condition as noted above in a mammal, including humans, suffering therefrom with a pharmaceutical composition having the compound of Formula I as defined above in unit dosage form. The invention also provides for use of any such compound of Formula I or salt thereof in the manufacture of a medical therapeutic agent.

A pharmaceutical composition of Formula I or use of the compound of Formula I is meant to include treatment understood to be prophylactic pertinent to the foregoing named conditions.

The more preferred compounds of the present invention are those of the Formula I wherein $R_1$ is hydrogen, methyl or phenyl.

Most preferred are:
N-[1-[3,5 bis(1,1-dimethylethyl)-4-hydroxyphenyl]ethyl]-N hydroxy-2-methylpropanamide;
N-[1-[3,5-bis(1,1 dimethylethyl)-4-hydroxyphenyl]ethyl]-N-hydroxyacetamide;
[1-[3,5-bis(1,1-dimethylethyl)-4-hydroxyphenyl]ethyl]-hydroxycarbamic acid, ethyl ester;
N-[1-[3,5-bis(1,1 dimethylethyl)-4-hydroxyphenyl]ethyl]-N hydroxy-N'-methylthiourea;

N-[1-[3,5-bis(1,1 dimethylethyl)-4-hydroxyphenyl]ethyl]-N-hydroxy-N'-methylurea;

N-[1-[3,5-bis(1,1 dimethylethyl)-4-hydroxyphenyl]ethyl]-N'-ethyl-N-hydroxyurea;

N-[1-[3,5-bis(1,1 dimethylethyl)-4-hydroxyphenyl]ethyl]- N-hydroxyurea;

[[[1-[3,5-bis(1,1-dimethylethyl)-4-hydroxyphenyl]ethyl]hydroxyamino]-thioxomethyl]carbamic acid, ethyl ester, acetate;

N-(acetyloxy) N-[[3,5-bis(1,1-dimethylethyl)-4-hydroxyphenyl]methyl]acetamide;

N-[[3,5-bis(1,1-dimethylethyl)-4-hydroxyphenyl]methyl]-2-methyl-N-[2-methyl-1-oxopropoxy]-propanamide;

N-[[3,5-bis(1,1-dimethylethyl)-4-hydroxyphenyl]methyl]-N-hydroxy-2-methylpropanamide;

N-[[3,5-bis(1,1-dimethylethyl)-4-hydroxyphenyl]methyl]acetamide;

2,6-bis(1,1-dimethylethyl)-4-[(methoxyamino)phenylmethyl]phenol, monohydrochloride;

2,6-bis(1,1-dimethylethyl)-4-[(hydroxymethylamino)-phenylmethyl]phenol monohydrochloride;

2,6-bis(1,1-dimethylethyl)-4-[hydroxyamino)phenylmethyl]phenol;

N-[[3,5-bis(1,1-dimethylethyl)-4-hydroxyphenyl]-phenylmethyl]-N-hydroxy-2-methylpropanamide;

N-[[3,5-bis(1,1-dimethylethyl)-4-hydroxyphenyl]-phenylmethyl]-N-hydroxyacetamide;

[3,5-bis(1,1-dimethylethyl)-4-hydroxyphenyl]phenylmethyl]hydroxycarbamic acid, ethyl ester;

N-[[3,5-bis(1,1-dimethylethyl)-4-hydroxylphenyl]-phenylmethyl]-N'-ethyl-N-hydroxyurea;

N-[[3,5-bis(1,1-dimethylethyl)-4-hydroxyphenyl]-phenylmethyl]-N-hydroxy-N'-methylurea;

N-[[3,5-bis(1,1-dimethylethyl)-4-hydroxyphenyl]-phenylmethyl]-N-hydroxy-N'-methylthiourea; and N-[[3,5-bis(1,1-dimethylethyl)-4-hydroxyphenyl]-phenylmethyl]-N-hydroxyurea.

DETAILED DESCRIPTION OF THE INVENTION

In compounds of Formula I, the term "lower alkyl" includes a straight or branched alkyl group of from one to six carbons such as methyl, ethyl, propyl, (methyl)ethyl, (methyl)propyl, butyl, (dimethyl)ethyl, and the like.

"Lower alkoxy" includes a straight or branched alkoxy group of from one to six carbons as in alkyl defined above such as methoxy, ethoxy, propoxy, butoxy and the like.

"Halogen" is chloro, bromo, or fluoro.

"5- or 6 heterocycle wherein the heterocycle is a saturated ring having one to three heteroatoms selected from nitrogen, oxygen and sulfur" includes 2 or 3-tetrahydrofuranyl, 2- or 3-tetrahydrothienyl, 2- or 3-tetrahydropyranyl, 2-, 3-, or 4-piperadinyl, 3- or 4-pyrazolidinyl, 2-, 4-, or 5-thiazolidinyl, 2- or 3-piperazinyl, 2- or 3-morpholinyl, or 3- or 4-hexahydropyridazinyl and the like.

"Alkanoyl of from two to four atoms" is acetyl, propionyl, butyryl, or branched isomers thereof.

Appropriate compounds of Formula I are useful in free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as ethanesulfonic acid and benzenesulfonic acid, p-toluenesulfonic acid, and the like, giving the hydrochloride, sulfate, ethanesulfonate, benzenesulfonate, p-toluenesulfonate, and the like, respectively; or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; chlorine; guanidine; N-methyl glucosamine; n-methyl glucamine; l-glutamine; N-methylpiperazine; morpholine; ethylene diamine; N-benzylphenethylamine; tris(hydroxymethyl) aminoethane; and the like (see for example, "Pharmaceutical Salts", *J. Pharm. Sci.* 66(1):1–19 (1977)). Salts of inorganic bases include sodium, potassium, calcium, or the like.

The acid addition salts of said basic compounds are prepared either by dissolving the free base or acid of compound I in an aqueous or aqueous alcohol solution or other suitable solvent containing the appropriate acid or base, and isolating the salt by evaporating the solution or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of this invention may also exist in hydrated or solvated forms.

Thus, pharmaceutical compositions are prepared from compounds of Formula I and salts thereof described as the present invention in unit dosage form comprising the compound either alone or in admixture with a pharmaceutically acceptable carrier appropriately selected from those known.

In determining when a lipoxygenase, cyclooxygenase, or dual lipoxygenase/cyclooxygenase inhibitor is indicated, of course, inter alia, the particular condition in question and its severity, as well as the age, sex, weight, and the like of the subject to be treated must be taken into consideration and this determination is within the skill of the attending physician or veterinarian.

A physician or veterinarian of ordinary skill readily determines a subject who is exhibiting allergic or inflammatory symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, cachets, lozenges, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an unaffected area (e.g., in the form of eye drops or by inhalation). For the treatment of allergic or inflammatory conditions such as erythema, the compounds of the present invention may also be administered topically in the form of ointments, creams, gels, or the like. In general, the preferred rout of administration is orally.

An effective but nontoxic quantity of the compound of Formula I or pharmaceutically acceptable salt thereof is employed in treatment. The dosage regimen is selected according to a variety of factors including condition of the subject to be treated, severity of symptoma, and the route of administration. In so proceeding, the physician or veterinarian could employ relatively low dosages at first, subsequently increasing the dose until a maximum response is obtained. For convenience, the total daily dosage may be divided and administered in portions during the day if desired.

Initial dosages of the compounds of the invention having Formula I or pharmaceutically acceptable salt thereof are ordinarily in the range of 20 mg up to 25 g per day, orally, preferably 50 mg to 350 mg per dose orally, given from one to four times daily or as needed. When other forms of administration are employed, equivalent doses are administered.

A suitable dose of a compound of Formula I or pharmaceutically acceptable salt thereof for a subject suffering from any condition as described hereinbefore is 0.1 $\mu$g to 500 mg of the compound per kilogram body weight. In the case of systemic administration, the dose may be in the range of 0.5 to 500 mg of the compound per kilogram body weight, the most preferred dosage being 0.5 to 500 mg per kilogram body weight administered two to three times daily. In the case of topical administration, e.g., to the skin or eye, a suitable dose may be in the range of 0.1 ng to 100 $\mu$g of the compound per kilogram body weight, typically about 0.1 $\mu$g/kg.

In the case of oral dosing for the treatment of prophylaxis of arthritis or inflammation in general, due to any cause, a suitable dose of a compound of Formula I or a pharmaceutically acceptable salt thereof, may be as specified in the preceding paragraph, but most preferably is from 1 to 5 mg of the compound per kilogram of body weight, for example, from 1 to 2 mg per kilogram body weight.

While it is possible for an active ingredient to be administered alone, it is preferable to present it as a pharmaceutical formulation comprising a compound of Formula I or a pharmaceutically acceptable acid addition or base salt thereof and a pharmaceutically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC WHOLE CELL 5-LIPOXYGENASE AND CYCLOOXYGENASE ASSAYS

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate-buffered saline, pH 7.4 (PBS; NaCl, 7.1 g; $Na_2HPO_4$, 1.15 g; $KH_2PO_4$, 0.2 g; and KCl, 0.2 g/L). Cells are finally suspended in PBS containing 1.0 mM calcium at a density of $2 \times 10^6$ cells/mL. Cells are incubated and without test agent (in DMSO) (1% DMSO is without effect on arachidonic acid metabolism) for 10 minutes at room temperature. Calcium ionophore A23187 (5 $\mu$M) is added and cells are incubated for 7 minutes at 37° C. The reaction is stopped by chilling the tubes on ice for 10 minutes. Cells are separated by centrifugation and the supernatant is stored at $-20°$ C. Aliquots (100 $\mu$L) are analyzed for $LTB_4$ and $PGF_{2\alpha}$ using radioimmunoassay kits as provided by the supplier.

Table 1 contains biochemical data for compounds of Formula I obtained from this whole cell assay as amount of inhibition at given $\mu$M or $IC_{50}$s which are calculated as the concentration of a test compound in micromoles ($\mu$M) causing 50% inhibition of $LTB_4$ or $PGF_{2\alpha}$ formation.

CARRAGEENAN-INDUCED RAT FOOT PAW EDEMA-2 (CFE-2) ASSAY: PROTOCOL

Carrageenan solution (1% w/v) is prepared by dissolving 100 mg carrageenan (Marine Colloidal Div., Springfield, N.J.) in 10 mL of sterile saline (0.9%) solution (Travenol). The solution is vortexed for 30 to 45 minutes. Animals are dosed with compound 1 hour before carrageenan challenge. Foot paw edema is induced by injecting 0.10 mL of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured 5 hours after carrageenan. The difference between the 5-hour and the initial paw volume is expressed as delta edema. The delta edema for each test group of animals is used to calculate the percent inhibition of edema achieved by the compound at the test dose compared with the vehicle control group. The $ID_{40}$ (the dose at which swelling is inhibited by 40%) is calculated by probit analysis for the dose at which 40% inhibition occurs.

MYCOBACTERIUM-INDUCED RAT FOOTPAD EDEMA ASSAY (MFE): PROTOCOL

*Mycobacterium butyricum* (5 mg/mL) is suspended in paraffin oil by sonication for 10 minutes in an ice bath.

Footpad edema is induced on Day 0 by injecting 0.1 mL of the Mycobacterium mixture into the left hindpaw of lightly anesthetized rats. Swelling in the injected hindpaw is determined by mercury plethysmography 72 hours after injection. Groups of rats are treated with test compounds (suspended in 0.5% hydroxypropyl methylcellulose with 0.2% Tween-80) or vehicle 1 hour before Mycobacterium injection and on Days 1 and 2. Inhibition of swelling is determined by comparing the change in hindpaw volume in compound- and vehicle treated rats. An $ID_{40}$ (the dose at which swelling is inhibited by 40%) is calculated by probit analysis.

GASTRIC ULCEROGENICITY (UD): PROTOCOL

Male outbred Wistar rats (100 to 250 g) are fasted for 24 hours. After fasting, test compounds are administered orally (in 2 mL/kg of 0.5% hydroxypropyl methylcellulose) and the rats are denied access to food and water for 6 more hours. The rats are then sacrificed with $CO_2$ so that the stomachs can be removed, opened along the greater curvature, and evaluated for the presence of gastric ulcers. Results are expressed as the percent of rats with gastric ulcers at a given dose or as the $UD_{50}$ (the dose which causes ulcers in 50% of the rats).

second active ingredient may be varied and will depend upon the effective dose of each ingredient. Generally, an effective dose of each will be used. Thus, for example, when a compound of the Formula I or II or salt thereof is combined with an NSAID, the weight ratio of the Formula I or salt thereof to the NSAID will generally range from about 100:1 to about 1:1000, preferably about 200:1 to 1:200. Combinations of a compound of the Formula I or II and other active ingredients will generally also be within the aforementioned range, but in each case, an effective dose of each active ingredient should be used.

Combinations of a compound of the Formula I or II or salt thereof and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprofen aluminum, indoprofen, ketoprofen, naproxen, benoxaprofen, flubiprofen, fenoprofen, fenbufen, pirprofen, earprofen, oxaprozin,

TABLE 1

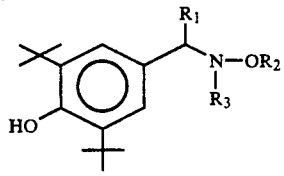

| Example Number | $R_1$ | $R_2$ | $R_3$ | ARBL $IC_{50}$ ($\mu M$) | ARBC $IC_{50}$ ($\mu M$) | CFE $ID_{40}$ mg/kg | MFE $ID_{40}$ mg/kg | $UD_{50}$ mg/kg |
|---|---|---|---|---|---|---|---|---|
| 12 | H | C(O)Me | C(O)Me | 95% @ 16[a] | N @ 16[d] | | | |
| 13 | H | C(O)iPr | C(O)iPr | 49% @ 16[a] | N @ 16[a] | | | |
| 14 | H | H | C(O)iPr | 95% @ 16[a] | N @ 16[d] | | | |
| 15 | H | H | C(O)Me | 90% @ 16[a] | N @ 16[d] | | | |
| 4 | Me | H | C(O)iPr | >91% @ 16[a] | N @ 16[d] | | | |
| 5 | Me | H | C(O)Me | >90% @ 16[a] | N @ 16[d] | | | |
| 6 | Me | H | C(O)OEt | >96% @ 16[a] | N @ 16[d] | | | |
| 10 | Me | H | C(O)NH$_2$ | 79% @ 16[a] | N @ 16[d] | | | |
| 8 | Me | H | C(O)NHMe | N @ 16[d] | 45% @ 16[b] | | | |
| 9 | Me | H | C(O)NHEt | >91% @ 16[a] | N @ 16[d] | | | |
| 7 | Me | H | C(S)NHMe | N @ 16[d] | N @ 16[d] | | | |
| 11 | Me | H | C(S)NHCOOEt (acetate salt) | 91% @ 16[a] | N @ 16[d] | | | |
| 20 | Ph | H | H (hydrochloride salt) | 2.3[c] | 4.1[c] | 13.2[c] | 3.8[c] | N @ 200[d] |
| 19 | Ph | H | Me | 1.2[c] | 4.3[c] | >30[c] | | |
| 18 | Ph | Me | H | 93% @ 10[a] | N @ 10[d] | | | |
| 22 | Ph | H | C(O)Me | 4.8[c] | 42/75% @ 16[b] | >30[c] | | |
| 21 | Ph | H | C(O)iPr | | | 5.3[c] | | |
| 25 | Ph | H | C(O)NHMe | 93% @ 16[a] | N @ 16[d] | | | |
| 26 | Ph | H | C(S)NHMe | 98% @ 16[a] | N @ 16[d] | | | |
| 24 | Ph | H | C(O)NHEt | 99% @ 16[a] | N @ 16[d] | | | |
| 23 | Ph | H | C(O)OEt | 97% @ 16[a] | N @ 16[d] | | | |
| 27 | Ph | H | C(O)NH$_2$ | 97% @ 10[a] | N @ 10[d] | | | |

[a]Inhibition of $LTB_4$ at given concentration
[b]Inhibition of $PGF_{2\alpha}$ at given concentration
[c]$IC_{50}$
[d]N = less than 40% inhibition at given concentration In addition to the compounds of Formula I or a pharmaceutically acceptable salt thereof, the pharmaceutical compositions can also contain other active ingredients, such as cyclooxygenase inhibitors, nonsteroidal antiinflammatory drugs (NSAIDs), peripheral analgesic agents such as zomepirac, diflunisol, and the like. The weight ratio of the compound of the Formula I to the pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, ioxepac, furofenac, tropinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH₂COOH group (which optionally can be in the form of a pharmaceutically acceptable salt group, e.g., —CH₂COO⁻Na⁺) typically attached directly to a ring system, preferably to an aromatic or heteroaromatic ring system.

Thus, "fenamic acid derivatives" as defined herein are nonnarcotic analgesics/nonsteroidal antiinflammatory drugs which contain the basic structure:

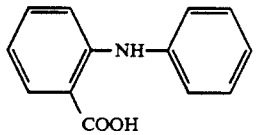

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

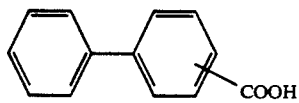

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam, and 4-hydroxy-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesic/nonsteroidal antiinflammatory drugs which have the general formula:

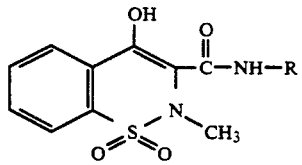

wherein R is an aryl or heteroaryl ring system.

The following NSAIDs may also be used: acemetacin, aminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fenetizole mesylate, fenclofenac, fenclorac, fendosal, fenflumizole, fentiazac, feprazone, floctafenine, flunixin, flunoxaprofen, fluproquazone, fopirtoline, fosfosal, furcloprofein, furofenac, flucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate, sodium, meseclazone, microprofen, nabumetone, nictinodole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudixocam, suprofen, talmetacin, talniflumate, tenoxicam, thiazolinobutazine, thielavin B, tiaprofenic acid, tiaramide HCl, tiflamazole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the Formula I compound or salt thereof may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compound of Formula I or salt thereof may also be advantageously combined with an H₁ or H₂-receptor antagonist, such as for instance, cimetidine, ranitidine, terfenadine, famotidine, temelastine, acrivastine, loratidine, utrizine, tazifylline, azelastine, aminothiadiazoles disclosed in European Patent 81102976.8 and like compounds such as those disclosed in U.S. Pat. Nos. 4,283,408; 4,362,736; 4,394,508; and European Patent Application 40,696. The pharmaceutical compositions may also contain a K⁺/H⁺-ATPase inhibitor such as omeprazole, disclosed in U.S. Pat. No. 4,255,431, and the like. Each of the references referred to in this paragraph is hereby incorporated by reference.

Generally, the scheme for the preparation of the compounds of Formula I above is shown in Scheme 1 and Scheme 2 as follows:

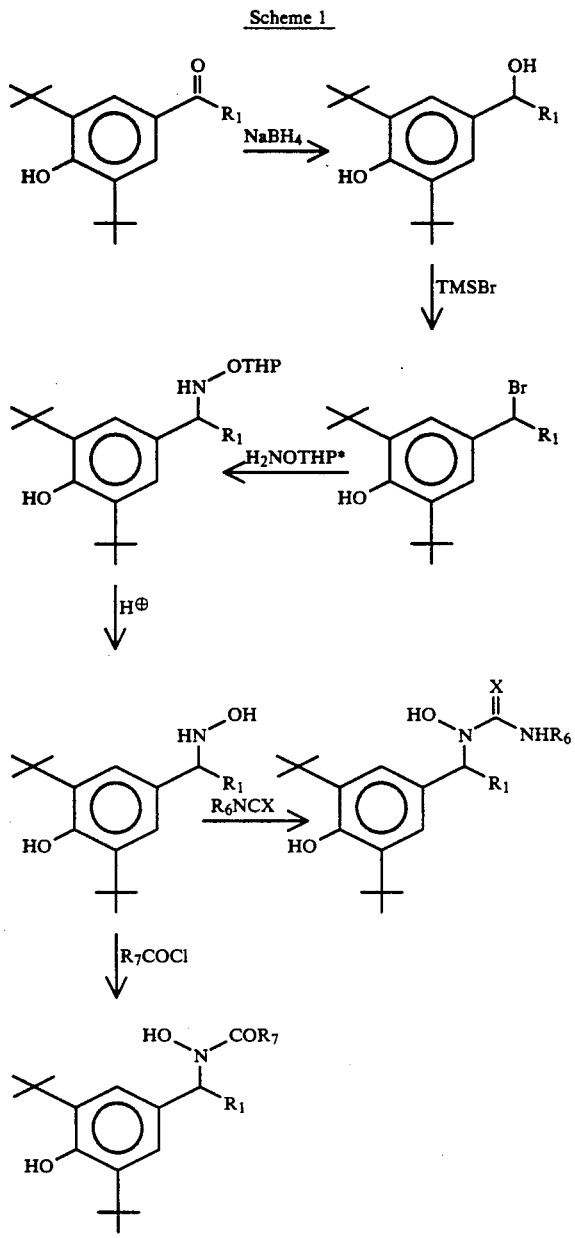

*THP is 2-tetrahydropyranyl.

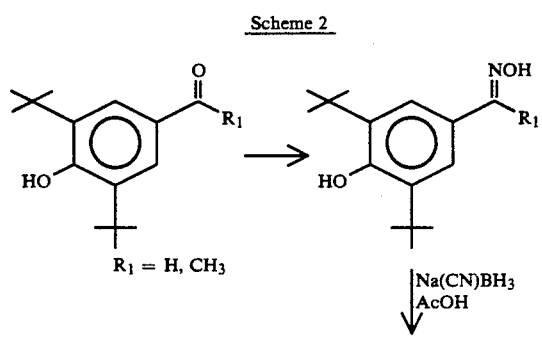

Conditions for carrying out the reactions within the description of Schemes 1 and 2 above an variations in the description are known or can be readily determined from analogous reactions known to one of ordinary skill in the art.

Those compounds that contain an acidic proton can be converted to salts via treatment with an organic or inorganic base according to known methods.

Generally, starting materials are known, commercially available, or can be prepared by known methods.

Under certain circumstances as discussed above, it is necessary to protect either the N or O of intermediates. Introduction and removal of such suitable oxygen and nitrogen protecting groups are well known in the art of organic chemistry; see for example, "Protective Groups in Organic Chemistry," J. F. W. McOmie, *Advances in Organic Chemistry* 3:159-190 (1963); J. F. W. McOmie, *Chem. & Ind.* 603 (1979), and T. W. Greene, "Protective Groups in Organic Synthesis," Wiley (New York) 1981, Chapters 2, 3, and 7.

Examples of suitable oxygen protecting groups are benzyl, t-butyl protecting groups, ethoxyethyl, methoxyethoxymethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethyl carbamate, trichloroethoxycarbonyl, vinyloxycarbamate acetyl, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis and t-butyldimethylsilyl being removed by reaction with, for example, tetra n-butylammonium fluoride.

In the process described herein for the preparation of compounds of this invention, the requirements for protective groups are generally well recognized by one skilled in the art of organic chemistry, and accordingly the use of appropriate protecting groups is necessarily implied by the processes of the schemes herein, although not expressly illustrated.

The products of the reactions described herein are isolated by conventional means such as extraction, distillation, chromatography, crystallization, and the like.

The invention is further elaborated by the representative examples as follows. Such examples are not meant to be limiting.

EXAMPLE 1

3,5-Bis(1,1-dimethylethyl)-4-hydroxyacetophenone oxime (Zh. Org. Khim. 23(11):2273-2280 (1987); CA 109(15):1281635

A mixture of 37.3 g (0.15 mole) of 3,5 bis(1,1-dimethylethyl)-4 hydroxyacetophenone, 34.7 g (0.50 mole) of hydroxylamine hydrochloride and 45 g (0.55 mole) of sodium acetate in MeOH (350 mL) is stirred at room temperature for 20 hours. The reaction mixture is evaporated to dryness and the residue is washed thoroughly with $H_2O$. The solid material is recrystallized from MeOH-THF-n-hexane to give 34.4 g (87%) of white crystals, m.p. 212°–215° C.

EXAMPLE 2

2,6-Bis(1,1-dimethylethyl) 4-[1-(hydroxyamino)ethyl]phenol acetate

Over an 18-minute period 31.4 g (0.5 mole $NaCNBH_3$ is added to 26.3 g (0.1 mole) of 3,5-bis (1,1-dimethylethyl)-4-hydroxyacetophenone oxime in HOAc (500 mL) while the temperature is maintained at 25° C. by means of an ice-water bath. After an additional 45 minutes at room temperature the reaction mixture is evaporated to dryness in a fume hood. The residue is treated with ice cold 2N NaOH (500 mL) and allowed to rise to room temperature when the pH is lowered to 5 with HOAc (100 mL). The precipitate is filtered off, washed with $H_2O$ and $Et_2O$, and recrystallized from HOAc-$Et_2O$ to give white crystals, 8.45 (32%), m.p. 150.5°–152° C. An additional 20 g of less pure product (but still satisfactory for synthetic purposes) is obtained by extraction of the aqueous filtrate with $Et_2O$.

EXAMPLE 3

2,6-Bis(1,1-dimethyl)-4-[1-(hydroxylamino)methyl]phenol is prepared as an oil according to the Example 2 using the corresponding benzaldehyde oxime.

EXAMPLE 4

N-[1-[3,5-Bis(1,1-dimethylethyl)-4-hydroxyphenyl]ethyl]-N-hydroxy-2-methylpropanamide A solution of 0.82 g (0.01 mole) of sodium acetate in $H_2O$ (7 mL) is added to a solution of 1.07 g (0.0033 mole) of 2,6-bis(1,1-dimethylethyl)-4-[1-(hydroxyamino)ethyl]phenol acetate (Example 2) in dioxane (35 mL). Isobutyryl chloride (0.488 g, 0.00458 mole) is added dropwise and the reaction mixture is stirred at room temperature for 16 hours. The reaction mixture is concentrated to half volume, diluted with $H_2O$, and extracted with $Et_2O$. The $Et_2O$ extracts are washed with saturated $NaHCO_3$, brine, dried over $Na_2SO_4$, and evaporated to dryness. The residue is recrystallized from n-hexane to give white crystals, 0.62 g (56%), m.p. 147°–148.5° C.

EXAMPLE 5

N-[1-[3,5-Bis(1,1-dimethylethyl)-4-hydroxyphenyl]ethyl]-N-hydroxyacetamide

The title compound is prepared by the method as in Example 4 by reaction with acetyl chloride. The product is recrystallized from n-hexane to give white crystals, 0.767 mg (66%), m.p. 153°–154° C.

EXAMPLE 6

[1-[3,5-Bis(1,1-dimethylethyl)-4-hydroxyphenyl]ethyl]-hydroxycarbamic acid, ethyl ester The title compound is prepared by the method as in Example 4 by reaction with ethyl chloroformate. The product is recrystallized from n hexane to give white crystals, 0.87 g (43%), m.p. 130°–132° C.

EXAMPLE 7

N-[1-[3,5-Bis(1,1-dimethylethyl)-4-hydroxyphenyl]ethyl]-N-hydroxy-N'-methylthiourea To a solution of 0.500 g (0.0016 mole) of 2,6-bis(1,1-dimethylethyl)-4-[1-(hydroxyamino)ethyl]phenol acetate is added 0.128 g (0.00175) of methyl isothiocyanate. The reaction mixture is stirred at room temperature for 18 hours and evaporated to near dryness. The residue is washed with $Et_2O$ and there is obtained 0.300 g (55%) white solid, m.p. 175°–175.5° C.

EXAMPLE 8

N-[1-[3,5-Bis(1,1-dimethylethyl)-4-hydroxyphenyl]ethyl]-N-hydroxy-N'-methylurea

The title compound is prepared by the method as in Example 7 by reaction with methyl isocyanate. The product is washed with $Et_2O$ and there is obtained white crystals, 0.567 g (35%), m.p. 159°–160° C.

EXAMPLE 9

N-[1-3,5-Bis(1,1-dimethylethyl)-4-hydroxyphenyl]ethyl]-N'-ethyl-N-hydroxyurea

The title compound is prepared by the method as in Example 7 by reaction with ethyl isocyanate. The product is recrystallized from n-hexane to give white crystals, 1.62 g (96%), m.p. 111° (dec 125°–130° C.).

EXAMPLE 10

N-[1-3,5-Bis(1,1-dimethylethyl)-4-hydroxyphenyl]ethyl]-N-hydroxyurea

To a solution of 0.814 g (0.0025 mole) of 2,6-bis(1,1-dimethylethyl)-4-[1-(hydroxyamino) ethyl]phenol acetate (Example 2) in THF (10 mL) is added 0.868 g (0.0075 mole) of 85% trimethylsilyl isocyanate. The reaction mixture is heated under reflux for 45 minutes and allowed to stand at room temperature for 16 hours. The mixture is poured into saturated $NH_4Cl$, concentrated to remove THF, extracted with EtOAc and dried over $Na_2SO_4$. The extracts are evaporated to dryness and the residue is recrystallized from $Et_2O$-n-hexane to give white crystals, 0.46 g (60%), m.p. 162°–163.5° C.

EXAMPLE 11

[[[1-[3,5-Bis(1,1-dimethylethyl)-4-hydroxyphenyl]ethyl]hydroxyamino]-thioxomethyl]carbamic acid, ethyl ester, acetate (10:3)

The title compound is prepared by the method as in Example 10 by reaction with ethoxycarbonyl isothiocyanate. The product is recrystallized from n-hexane to give white crystals, 0.89 g (64%), m.p. 108°–108.5° C.

EXAMPLE 12

N-(Acetyloxy)-N-[[3,5-bis(1,1-dimethylethyl)-4-hydroxyphenyl]methyl]acetamide, 0.3 hydrate A cooled solution (at −7° C.) of the hydroxylamine of Example 3 (5.9 g, 0.025 mol) in methylene chloride (150 mL) is treated with di-iso-propylethylamine (9.80 g, 0.075 mol) and stirred for 15 minutes before treating with acetyl chloride (3.90 g, 0.05 mol). The reaction mixture is stirred for 2.0 hours when the temperature reached 24° C. The reaction mixture is decomposed with 1N HCl (50 mL) and ice and then extracted with $CH_2Cl_2$, washed with water and dried ($Na_2SO_4$). Removal of solvent gives a pale yellow solid which is recrystallized from di-isopropylether. Yield 5.4 g (63%); m.p. 122°–127° C. Concentration of the mother liquor gives an additional amount of the product (0.81 g, total yield 73%).

EXAMPLE 13

N-[[3,5-Bis(1,1-dimethylethyl)-4-hydroxyphenyl]methyl]-2-methyl-N-[2-methyl-1-oxopropoxy]propanamide The title compound is prepared as in Example 12 as an oil which is purified by flash chromatography over silica gel using 5% EtOH toluene as eluant. Yield 7.38 g (94%); oil.

EXAMPLE 14

N-[[3,5-Bis(1,1-dimethylethyl) 4-hydroxyphenyl]methyl]-N-hydroxy-2-methyl-propanamide A solution of the ester amide of the Example 13 (1.35 g, 3.4 mM) in MeOH (60 mL) is treated with a suspension of $Ba(OH)_2$ (0.32 g, 1.6 mM) in MeOH (10 mL) and water (5.0 mL). The mixture is stirred at 24° C. for 72 hours when a pale green suspension is formed. It is carefully acidified with AcOH and filtered. The filtrate is evaporated to dryness and the residue diluted with water and extracted with $CH_2Cl_2$. The organic layer is worked up as usual to give an oil which is flash chromatographed over silica gel using n hexane and increasing amount of THF mixture as eluant to give the pure product as an oil (one spot on the TLC; ($SiO_2$; 20% THF hexane). Yield 0.53 g (49.5%).

EXAMPLE 15

N-[[3,5-Bis(1,1-dimethylethyl) 4-hydroxyphenyl]methyl]acetamide

The title compound is prepared as in Example 14 using the corresponding acetoxy-acetamide compound of Example 12. Yield 0.47 g (68%); m.p. 80°–84° C.

EXAMPLE 16

3,5-Bis(1,1-dimethylethyl)-4-hydroxy-α-phenylbenzenemethanol

Over a 25-minute period $NaBH_4$ (1.89 g, 0.05 mole) is added to a solution of 3.1 g (0.01 mole) of [3,5-bis(1,1-dimethylethyl)-4-hydroxyphenyl]phenylmethanone (C. D. Cook, JOC, 1960, p. 1429) in 50 mL absolute EtOH while maintaining the temperature at 10°–15° C. The reaction mixture is then allowed to come to room temperature for 1.5 hours. The reaction mixture is cooled t 0° and 4N HCl (12 mL) is slowly added. The white precipitate is filtered off and washed with $H_2O$. It is taken up in $Et_2O$ and washed with saturated $NaHCO_3$. After drying over $Na_2SO_4$ the $Et_2O$ is evaporated to dryness yielding an analytically pure olive colored product, 2.9 g (93%), m.p. 117°–119° C.

EXAMPLE 17

3,5 Bis(1,1-dimethylethyl)-4-hydroxy-α-phenylbenzyl bromide

To a solution of 31.2 g (0.1 mole) of 3,5-bis(1,1-dimethylethyl)-4-hydroxy-α-phenylbenzenemethanol (Example 16) in 350 mL of $CCl_4$ is added 34.8 (0.227 mole) of bromotrimethylsilane. After 40 minutes at room temperature the reaction mixture is evaporated to dryness on a rotary evaporator with the water bath temperature at 35° C. The brown oil residue is used immediately without further purification.

EXAMPLE 18

2,6-Bis(1,1-dimethylethyl)-4-[(methoxyamino)phenylmethyl]phenol, monohydrochloride Over a 20 minute period a solution of 3,5-bis(1,1-dimethylethyl)-4-hydroxy-α-phenylbenzyl bromide, Example 17, (6.23 g, 0.0166 mole) in 100 mL THF is added to a mixture of methoxylamine hydrochloride (4.18 g, 0.05 mole) and 5.62 g (0.0524 mole) of 2,6 lutidine in 175 mL THF. The reaction mixture is heated under reflux for 16 hours. An additional 5.62 g (0.0524 mole) of 2,6 lutidine and 2.0 g (0.0239 mole) of methoxylamine hydrochloride is added and reflux is continued for 24 hours. The mixture is evaporated to dryness and the residue is taken up in $Et_2O$, washed with $H_2O$, 1N HCl, saturated $NaHCO_3$ and brine. After evaporation to dryness the residue is treated with 5 mL of 20% ethereal HCl (w/v). Creamy white crystals form and are filtered off and recrystallized from $EtOAc$-$Et_2O$ to give an off-white solid, 3.6 g (57%), m.p. 183°–185° C.

EXAMPLE 19

2,6 Bis(1,1-dimethylethyl)-4-[(hydroxymethylamino)-phenylmethyl]phenol monohydrochloride The title compound is prepared by the method as in Example 18 by reaction with N methylhydroxylamine hydrochloride. The product is recrystallized from $EtOH$-$Et_2O$ to yield off white crystals, 2.4 g (42%), m.p. 166°–169° C.

EXAMPLE 20

2,6-Bis(1,1-dimethylethyl)-4-[hydroxyamino)phenylmethyl]phenol

Bromotrimethylsilane (1.1 g, 0.0072 mole) is added to a solution of 1.0 g (0.0032 mole) of 3,5-bis(1,1-dimethylethyl)-4-hydroxy-α-phenylbenzene methanol in $CCl_4$ (35 mL). After 30 minutes at room temperature the mixture is evaporated to dryness. The residue is taken up in THF (50 mL) and 1.4 g (0.012 mole) of hydroxylamine tetrahydropyran ether is added. The mixture is heated under reflux for 1 hour and then allowed to stand at room temperature for 16 hours. Conc. HCl (2 mL) is added and the mixture is heated at 55° C. for 45 minutes and evaporated to dryness. The residue is taken up in $Et_2O$ and washed with $H_2O$, 1N HCl, saturated $NaHCO_3$, brine, and dried over $Na_2SO_4$. After evaporation to dryness the crude product is filtered through a column of flash silica gel 60 (230–400 mesh) eluting with CH₂Cl₂. The product fractions are recrystallized from cyclohexane pentane yielding white crystals, 0.29 g (24%), m.p. 135°–137° C.

EXAMPLE 21

N-[3,5-Bis(1,1-dimethylethyl)-4-hydroxyphenyl]-phenylmethyl]-N-hydroxy-2-methylpropanamide A solution of 0.82 g (0.01 mole) of sodium acetate in 7 mL H₂O is added to a solution of 1.08 g (0.0033 mole) of 2,6 bis(1,1 dimethylethyl)-4-[(hydroxyamino)phenylmethyl]phenol in 30 mL dioxane. Isobutyryl chloride (0.51 g, 0.00477 mole) is added dropwise and the mixture is stirred at room temperature for 17 hours. Water (25 mL) is added to the mixture and the solid material is filtered off and washed with water. After drying it is recrystallized from Et₂O n-hexane to give off white crystals, 0.477 g (36%), m.p. 179°–180° C.

EXAMPLE 22

N-[[3,5-Bis(1,1-dimethylethyl)-4-hydroxyphenyl]-phenylmethyl]-N-hydroxyacetamide By the method as in Example 21 acetyl chloride is used to prepare the title compound. Recrystallization from n-hexane gave 0.41 g (60%) white crystals, m.p. 163.5°–166° C.

EXAMPLE 23

[3,5-Bis(1,1-dimethylethyl)-4-hydroxyphenyl]phenylmethyl]hydroxycarbamic acid, ethyl ester By the method as in Example 21 ethyl chloroformate is used to prepare the title compound. Recrystallization from Et₂O gave 0.94 g (47%) off-white crystals, m.p. 152°–154° C.

EXAMPLE 24

N-[[3,5-Bis(1,1-dimethylethyl)-4-hydroxylphenyl]-phenylmethyl]-N'-ethyl-N-hydroxyurea Ethyl isocyanate (0.404 g, 0.0057 mole) is added to a solution of 1.64 g (0.005 mole) of 2,6 bis(1,1-dimethylethyl)-4-[(hydroxyamino)phenylmethyl]phenol in 50 mL toluene. After stirring at room temperature for 30 minutes the reaction mixture is concentrated to half its volume (rotary evaporator) and diluted with n-hexane. The solid is filtered off, washed with n-hexane, and recrystallized from Et₂O-cyclohexane to give white crystals, 1.35 g (68%), m.p. 158°–159.5° C.

EXAMPLE 25

N-[[3,5-Bis(1,1-dimethylethyl)-4-hydroxyphenyl]-phenylmethyl]-N-hydroxy-N'-methylurea By the method as in Example 24 methyl isocyanate is used to prepare the title compound. The crude product is washed with n-hexane to give 1.6 g (83%) of white solid, m.p. 171.5°–172.5° C.

EXAMPLE 26

N-[[3,5-Bis(1,1-dimethylethyl)-4-hydroxyphenyl]-phenylmethyl]-N-hydroxy-N'-methylthiourea By the method as in Example 24 methyl isothiocyanate is used to prepare the title compound. The crude product is washed with n hexane to give 1.05 g (88%) white solid, m.p. 158°–159.5° C.

EXAMPLE 27

N-[[3,5-Bis(1,1-dimethylethyl)-4-hydroxyphenyl]-phenylmethyl]-N-hydroxyurea

Trimethylsilyl isocyanate (0.58 g, 0.005 mole) is added to a solution of 0.98 g (0.003 mole) of 2,6-bis(1,1-dimethylethyl)-4-[(hydroxyamino)phenylmethyl]-phenol in 15 mL THF. The reaction mixture is heated under reflux for 30 minutes then stirred at room temperature for 17 hours. The reaction mixture is poured into saturated NH₄Cl and concentrated on the rotary evaporator to remove some THF. Following dilution with H₂O the mixture is extracted with EtOAc and the extracts are washed with brine, dried over Na2SO4, and evaporated to dryness. The residue is recrystallized from Et₂O-n-hexane to give off white crystals, 0.53 g (47%), m.p. 188°–189° C.

We claim:

1. A compound of the Formula (I)

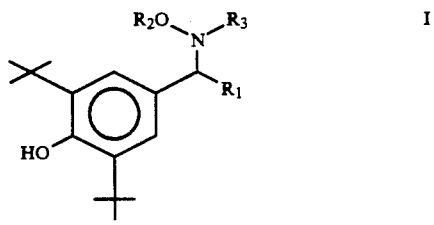

or a pharmaceutically acceptable salt thereof; wherein $R_1$ is
  1) hydrogen;
  2) methyl;
  3) phenyl optionally substituted by from one to three of i) hydrogen, ii) halogen, iii) trifluoromethyl, iv) lower alkyl, v) lower alkoxy, and vi) hydroxy;

$R_2$ is
  1) hydrogen;
  2) alkanoyl of from two to four carbon atoms; or
  3) lower alkyl;

$R_3$ is
  1) hydrogen;
  2) lower alkyl;
  3) alkanoyl of from two to four carbon atoms; or
  4) $COR_7$ or $COOR_7$ is lower alkyl.

2. A compound of claim 1 wherein $R_1$ is hydrogen, methyl, or phenyl.

3. A compound of claim 1 which is N-[1-[3,5-bis(1,1-dimethylethyl)-4-hydroxyphenyl]ethyl]-N-hydroxy-2-methylpropanamide.

4. A compound of claim 1 which is N-[1-[3,5-bis(1,1-dimethylethyl)-4-hydroxyphenyl]ethyl]-N-hydroxyacetamide.

5. A compound of claim 1 which is [1-[3,5-bis(1,1-dimethylethyl)-4-hydroxyphenyl]ethyl]-hydroxycarbamic acid, ethyl ester.

6. A compound of claim 1 which is N-(acetyloxy)-N-[[3,5-bis(1,1-dimethylethyl)-4-hydroxyphenyl]methyl]acetamide.

7. A compound of claim 1 which is N-[[3,5-bis(1,1-dimethylethyl)-4-hydroxyphenyl]methyl]-2-methyl-N-[2-methyl-1-oxopropoxy]propanamide.

8. A compound of claim 1 which is N-[[3,5-bis(1,1-dimethylethyl)-4-hydroxyphenyl]methyl]-N-hydroxy-2-methylpropanamide.

9. A compound of claim 1 which is N-[[3,5-bis(1,1-dimethylethyl)-4 hydroxyphenyl]methyl]acetamide.

10. A compound of claim 1 which is 2,6-bis(1,1-dimethylethyl)-4-[(methoxyamino)phenylmethyl]phenol, monohydrochloride.

11. A compound of claim 1 which is 2,6-bis(1,1-dimethylethyl)-4-[(hydroxymethylamino)phenylmethyl]phenol, monohydrochloride.

12. A compound of claim 1 which is 2,6-bis(1,1-dimethylethyl)-4-[hydroxyamino)phenylmethyl]phenol.

13. A compound of claim 1 which is N-[[3,5-bis(1,1-dimethylethyl)-4-hydroxyphenyl]phenylmethyl]-N-hydroxy-2-methylpropanamide.

14. A compound of claim 1 which is N-[[3,5 bis(1,1-dimethylethyl)-4-hydroxyphenyl]phenylmethyl]-N-hydroxyacetamide.

15. A compound of claim 1 which is [3,5-bis(1,1-dimethylethyl)-4-hydroxyphenyl]phenylmethyl]hydroxycarbamic acid, ethyl ester.

16. A pharmaceutical composition for the treatment of arthritis and inflammation which comprises an antiarthritic or antiinflammatory effective amount of a compound of claim 1 together with a pharmaceutically acceptable carrier.

17. A method for the treatment of arthritis and inflammation in a human comprising administering a compound of claim 1 in unit dosage form.

* * * * *